United States Patent [19]
DiIorio et al.

[11] Patent Number: 5,442,289
[45] Date of Patent: Aug. 15, 1995

[54] BIOMAGNETOMETER HAVING FLEXIBLE SENSOR

[75] Inventors: Mark S. DiIorio, Del Mar; Eugene C. Hirschkoff, Leucadia; Richard T. Johnson, San Diego; D. Scott Buchanan, Escondido; Stephen O. James, San Diego; Douglas Paulson; William C. Black, Jr., both of Del Mar, all of Calif.

[73] Assignee: Biomagnetic Technologies, Inc., San Diego, Calif.

[21] Appl. No.: 967,217

[22] Filed: Oct. 27, 1992

Related U.S. Application Data

[63] Continuation-in-part of Ser. No. 551,841, Jul. 17, 1990, Pat. No. 5,158,932, which is a continuation-in-part of Ser. No. 386,948, Jul. 31, 1989, Pat. No. 5,061,680, and a continuation-in-part of Ser. No. 831,905, Feb. 6, 1992.

[51] Int. Cl.$^6$ ............... G01R 33/035; A61B 5/05; H01F 6/06
[52] U.S. Cl. ................ 324/248; 128/653.1; 505/162; 505/220; 505/705; 505/846
[58] Field of Search ............ 324/228, 244, 248, 260; 128/653.1; 505/162, 220, 705, 846

[56] References Cited

U.S. PATENT DOCUMENTS

| | | | |
|---|---|---|---|
| 3,731,184 | 5/1973 | Goldberg et al. | 324/239 |
| 4,771,239 | 9/1988 | Hoenig | 324/248 |
| 4,906,930 | 3/1990 | Nakane et al. | 324/248 |
| 4,951,674 | 8/1990 | Zanakis et al. | 128/653.1 |
| 4,982,158 | 1/1991 | Nakata et al. | 324/248 X |
| 4,996,479 | 2/1991 | Hoenig | 324/248 |
| 5,008,622 | 4/1991 | Overton, Jr. et al. | 324/248 |
| 5,061,680 | 10/1991 | Paulson et al. | 324/248 X |
| 5,309,095 | 5/1994 | Ahonen et al. | 324/248 |
| 5,323,777 | 6/1994 | Ahonen et al. | 324/248 X |

FOREIGN PATENT DOCUMENTS

| | | | |
|---|---|---|---|
| 516955 | 10/1976 | U.S.S.R. | 324/228 |
| 667922 | 6/1979 | U.S.S.R. | 324/228 |
| WO89/12833 | 12/1989 | WIPO | |

Primary Examiner—Gerard R. Strecker
Attorney, Agent, or Firm—Gregory Garmong

[57] ABSTRACT

A biomagnetometer includes a magnetic field sensor unit having a magnetic field pickup coil. A vessel contains the sensor unit. The vessel includes a flexible contact face with the magnetic field sensor unit mounted in the interior of the vessel adjacent to the flexible contact face. Insulation at the flexible contact face of the vessel prevents excessive heat flow through the flexible contact face. Pickup units using this structure can be connected together into flexible or rigid arrays. In operation, the pickup coil is cooled to a temperature of less than its superconducting transition temperature. A detector measures the magnitude of magnetic fields sensed by the sensor unit.

20 Claims, 7 Drawing Sheets

BIOMAGNETOMETER HAVING FLEXIBLE SENSOR

BACKGROUND OF THE INVENTION

This application is a continuation-in-part of application Ser. No. 07/551,841, filed Jul. 17, 1990, now U.S. Pat. No. 5,158,932, for which priority is claimed, which is a continuation-in-part of application Ser. No. 07/386,948, filed Jul. 31, 1989, now U.S. Pat. No. 5,061,680, for which priority is claimed. This application is also a continuation-in-part of pending application Ser. No. 07/831,905, filed Feb. 6, 1992, for which priority is claimed.

This invention relates to apparatus for the measurement of biomagnetic signals produced by the body, and, more particularly, to such apparatus in which the magnetic pickup coils are provided in a flexible container.

The human body produces various kinds of energy that may be used to monitor the status and health of the body. Perhaps the best known of these types of energy is heat. Most healthy persons have a body temperature of about 98.6 F. A measured body temperature that is significantly higher usually indicates the presence of an infection or other deviation from normal good health. A simple medical instrument, the clinical thermometer, has long been available to measure body temperature.

Over 100 years ago, medical researchers learned that the body also produces electrical signals. Doctors today can recognize certain patterns of electrical signals that are indicative of good health, and other patterns that indicate disease or abnormality. The best known types of electrical signals are those from the heart and from the brain, and instruments have been developed that measure such signals. The electrocardiograph measures electrical signals associated with the heart, and the electroencephalograph measures the electrical signals associated with the brain. Such instruments have now become relatively common, and most hospitals have facilities wherein the electrical signals from the bodies of patients can be measured to determine certain types of possible disease or abnormality.

More recently, medical researchers have discovered that it is possible to measure the magnetic fields which are produced by the electrical currents that flow in the body. The research on correlating magnetic fields with various states of health, disease and abnormality is underway, but sufficient information is available to demonstrate that certain emitted magnetic fields are associated with abnormal conditions. Medical studies are investigating the nature of the normal and abnormal magnetic fields of the brain and heart, and seeking to correlate those fields with body functions and patient health.

For example, if it were known that a particular abnormality, such as epilepsy, stroke, or cardiac arrhythmia, were associated with an abnormal magnetic field produced at a particular location in the body, it might be possible to detect the abnormality at an early stage, while it was treatable, and then apply other medical knowledge to chemically treat or surgically remove that precise portion of the body with minimal side effects on the patient. Magnetic studies of the brain and heart therefore offer the potential for understanding and treating some of tile most crippling diseases and conditions known.

The biomagnetometer is an instrument that measures magnetic fields produced by the body, particularly the brain and heart. The biomagnetometer is a larger, more complex instrument than the medical instruments mentioned earlier, primarily because the magnetic fields produced by the body are very small and difficult to measure. Typically, the strength of the magnetic field produced by the brain is about 0.000000001 Gauss, at a distance of 1–2 centimeters from the head. The strength of the magnetic field produced by the heart is about 100 times larger. By comparison, the strength of the earth's magnetic field is about 0.5 Gauss, or about five hundred million times larger than the strength of the magnetic field produced by the brain, as measured externally to the head. Most electrical equipment also produces magnetic fields, in many cases much larger than that of the earth's field. It is apparent that, unless special care is taken, it is not possible to make magnetic measurements of the human body because the external influences such as the earth's magnetism and nearby apparatus can completely overwhelm and mask the magnetic fields from the body.

The biomagnetometer includes a magnetic field pickup coil connected to a very sensitive detector of the electrical signals produced by the magnetic signals sensed by the pickup coil. The currently most widely used detector is a Superconducting QUantum Interference Device or SQUID, which, in combination with a superconducting pickup coil, is sufficiently sensitive to detect magnetic signals produced by the brain. (See, for example, U.S. Pat. Nos. 4,386,361, 4,403,189, and 5,194,117, whose disclosures are incorporated by reference, for descriptions of various types of SQUIDs.) The detector, pickup coil, and their associated equipment require special operating conditions such as a cryogenic dewar, and cannot be placed into the body or attached directly to the surface of the body. In the current instrument, the dewar is operated at liquid helium temperature (about 4.2K), to maintain the SQUID detector, the pickup coil, and the electrical connection between them in the superconducting state. Only when the pickup coil, SQUID detector, and interconnections are superconducting can the biomagnetometer detect the magnetic fields produced by the small electrical currents of the body.

The conventional biomagnetometer therefore includes a dewar structure in which the pickup coil, the SQUID detector, and the electrical interconnects are cooled by liquid helium. The dewar normally is constructed with a small-diameter "tail" section, which permits placement of the pickup coil in close proximity to the patient, typically less than about 2 centimeters away. (See U.S. Pat. No. 4,773,952, whose disclosure is incorporated by reference, for a description of the construction of the dewar.) Special electronics is provided to attenuate external effects such as the earth's magnetic field and the magnetic fields of nearby electrical instruments. (For a description of such a device, see U.S. Pat. Nos. 3,980,076 and 4,079,790, whose disclosures are herein incorporated by reference.) The patient and detector can also be placed into a magnetically quiet enclosure that shields the patient and the detector from the external magnetic fields. (For a description of such an enclosure, see U.S. Pat. No. 3,557,777, whose disclosure is herein incorporated by reference.) With these special precautions, medical researchers and doctors can now make accurate, reliable measurements of the magnetic fields produced by the brain and by the heart, and are studying the relationship of these fields with diseases and abnormalities.

The existing approach of enclosing the pickup coil and the SQUID detector in a liquid-helium dewar is acceptable in many circumstances. Nevertheless, it would be desirable to have another approach wherein the physical size of the equipment could be reduced, to permit more flexibility in the use of the biomagnetometer. It would also be desirable to permit larger arrays of pickup coils to be placed closer to larger regions of the individual subjects' heads or chests than is now possible. The heads of subjects vary greatly in size and shape, and the existing approach can only be used for relatively small areas of the head at one time. The present invention fulfills these needs, and further provides related advantages.

SUMMARY OF THE INVENTION

The present invention provides a construction for a biomagnetometer having an array of magnetic field pickup coils that is much more easily manipulated into place adjacent a subject than was previously possible, because it is held in a flexible container. In the new approach, the pickup coils may be placed closer to the subject, and thence closer to the source of the magnetic field, than possible with the prior approach. Larger numbers of pickup coils may be placed close to a greater variety of patients whose head sizes and shapes vary substantially from one patient to another, and who may be wearing bandages or other medical appliances.

In accordance with the invention, a biomagnetometer includes a magnetic field sensor unit. The sensor unit has a magnetic field pickup coil made of a material having a superconducting transition temperature. There is a vessel means for containing the magnetic field sensor unit, the vessel means including a flexible contact face with the magnetic field sensor unit mounted in the interior of the vessel mean s adjacent to the flexible contact face. Insulation means at the flexible contact face of the vessel means prevents excessive heat flow through the flexible contact face. A number of such vessels and their contained sensor units may be mechanically connected together either flexibly or rigidly to form an array. There is additionally a means for cooling the pickup coil to a temperature of less than its superconducting transition temperature, and a detector means for measuring the magnitude of magnetic fields sensed by the sensor unit.

The pickup coils are preferably made of "high Tc" material, material that becomes superconducting at critical temperature (Tc) of at least 77K, and preferably at even higher temperature. The pickup coils need only be cooled to a few degrees Kelvin below their Tc value to be operable. It is far easier to cool such pickup coils and maintain them at 77K or higher, or at intermediate temperatures between 10K and 77K, than to cool and maintain them at lower temperatures such as 10K or below as required for conventional biomagnetometers. Significantly, less insulation is required to maintain such pickup coils at their superconducting temperatures. Many materials of construction become brittle at low temperatures, and operating at temperatures above 77K decreases the likelihood of a failure of these materials. The pickup coils may therefore be placed close to the interior wall of a flexible container that can be reshaped to fit to the contour of the body of the subject. Thus, the pickup coils are closer to the source of the magnetic fields than previously possible both because the container wall can be made thin (because less insulation is required) and because the entire container can be reshaped to conform to the surface of the body immediately above the source of the magnetic fields. The flexible container is insulated to maintain the pickup coils below their Tc, to prevent chilling of the subject, and for cryogenic efficiency.

Each pickup coil and its detector may be provided on the same support or in different parts of the same container to operate them at essentially the same temperature. Alternatively, they may be placed into different containers and maintained at different superconducting temperatures. The structure having provision for two superconducting temperatures allows the pickup coil to be positioned remotely from the detector, which results in major advantages from the standpoint of the practical utilization of the biomagnetometer in those cases where the detector must be operated at temperatures below the operating temperature of the pickup coil, and typically at temperatures near absolute zero.

With the discovery of superconductors having superconducting transition temperatures above 77K, the biomagnetometer of the invention can be constructed with the pickup coil and the electrical connector of a material having a superconducting transition temperature above 77K, the boiling point of liquid nitrogen. The pickup coil may be remotely placed and maintained below its superconducting transition temperature, and the electrical connector may also be readily maintained below its superconducting transition temperature.

The detector may still be maintained at an acceptable operating temperature, which may be near absolute zero or at some higher temperature. SQUIDs fabricated from materials which become superconducting at higher temperatures while maintaining high sensitivity would permit the detector to be operated at a higher temperature than 10K, and possibly even higher than 77K. Both the magnetic pickup coils and the detector may be operated at relatively high temperature, and even at the same high temperature, but physically separated in the manner disclosed herein.

In one preferred approach the detector remains essentially stationary, and the pickup coil is readily moved about while remaining tethered to the detector. The detector always stays at its operating temperature, while an electrical connector and thermal connector in the tether may be disconnected to replace the pickup coil with another design of pickup coil without serious thermal interruption to the apparatus. In another preferred approach, the detector coils and SQUIDs are both made of high-Tc materials and are packaged together inside the same flexible container.

Other features and advantages of the invention will be apparent from the following more detailed description of the preferred embodiment, taken in conjunction with the accompanying drawings, which illustrate, by way of example, the principles of the invention.

DETAILED DESCRIPTION OF THE INVENTION

Figure 1:
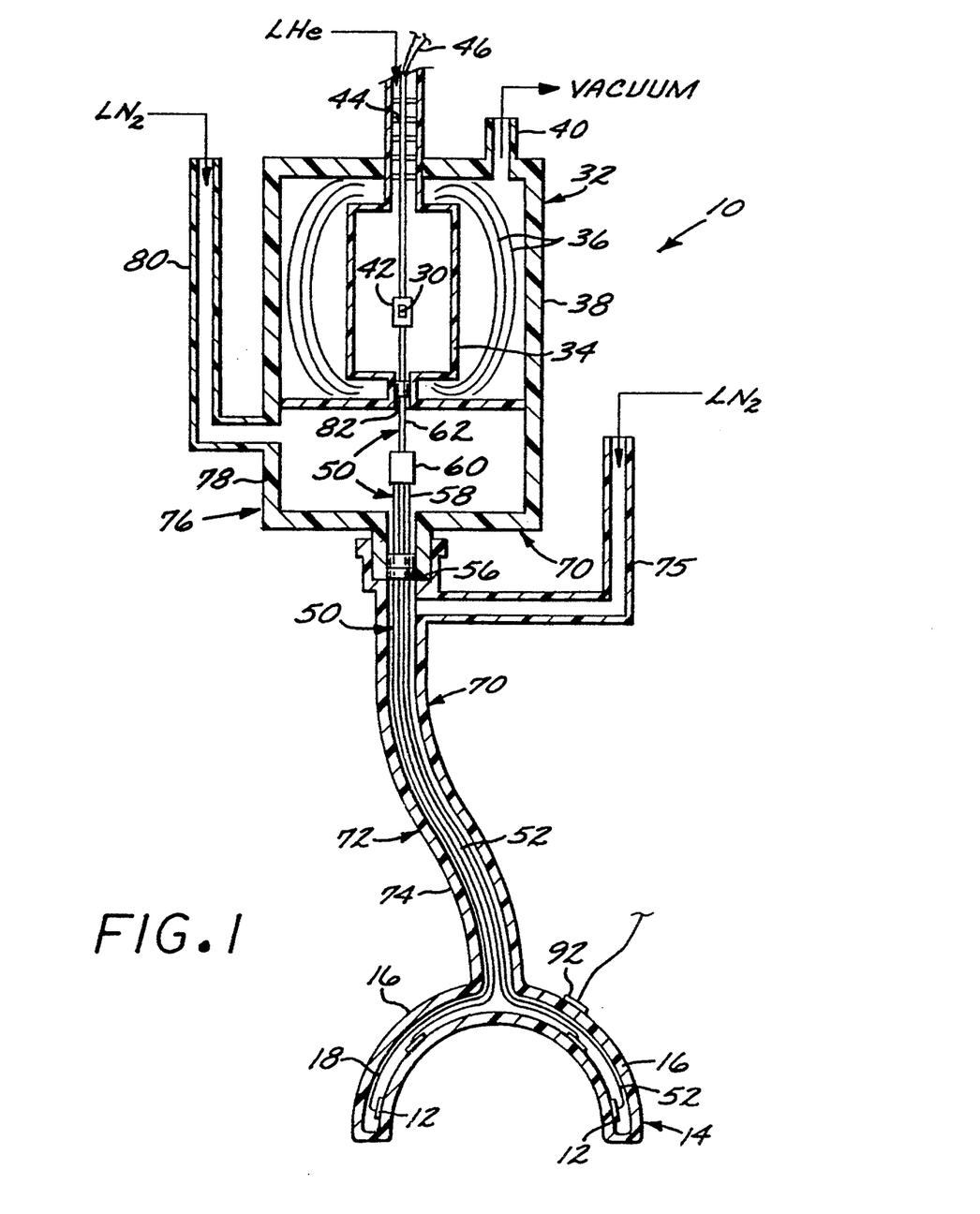
FIG. 1 is a side sectional view of a biomagnetometer apparatus.

A biomagnetometer 10 is illustrated in FIG. 1. In this biomagnetometer 10, the magnetic field pickup coils are maintained and operated at a different temperature than the detectors. The biomagnetometer 10 includes a number of pickup coils 12 in a first container 14. The pickup coil 12 is formed of a material having a superconducting transition temperature of greater than 77K. The presently preferred material of construction of the pickup coil 12 is $YBa_2Cu_3O_{7-x}$, where x is typically about 0.1–0.2, depending upon the fabrication approach of the oxide. This material has been demonstrated to have a superconducting transition temperature of greater than 77K. Other materials having superconducting transition temperatures greater than 77K are also acceptable. Some examples include $Bi_2Ca_2Sr_2 Cu_3O_{10}$ and $Tl_2Ba_2Ca_2Cu_3O_{10}$. As used herein, the "superconducting transition temperature" (Tc) is the highest temperature at which the material becomes superconducting, in the absence of an applied magnetic field.

When small, low frequency magnetic fields are to be received by a pickup coil, the coil must be maintained in the superconducting state to permit the current generated by the small magnetic field variations to flow freely and not be dissipated as ohmic heating, and to eliminate noise due to the dissipation process. It is not required that the pickup coil be maintained at a temperature near absolute zero, and therefore the construction of the pickup coil from "high temperature superconductors" having superconducting transit ion temperatures at or above 77K is acceptable. Construction of the pickup coil from high temperature superconductors is not required, and more conventional low-temperature superconductors such as niobium (having a Tc below 77K) may instead be used in a less preferred embodiment.

The container 14 is formed as an insulated vessel 16 having an interior volume 18 for containing liquid nitrogen or other liquefied gas, or a refrigerated gas, as a coolant. The walls of the vessel 16 can be made of rigid materials such as fiberglass or insulating foam, a construction well known in the industry for making liquid nitrogen dewars. The walls of the vessel 16 can also be made of flexible materials such as corrugated stainless steel in the form of an elongated, double walled tube, or supported membranes such as plastics. Such flexible metal construction is well known in the industry for transfer tubes used to move cryogenic liquids. A thin membrane construction is known in the industry to protect against intense cold, as in aerospace applications. The walls of the vessel 16 can also be made of a composite construction, wherein part is rigid and part is flexible. With this approach, some portions of the walls of the vessel 16 can be made of a thin rigid material such as fiberglass, and other portions could be made of a flexible material so that the container 14 could be reshaped to conform to the body of the subject. The insulated walls of the vessel 16 prevent discomfort from the cold for the human subject contacted with the surface of the container 14. Details of the design of the pickup coils 12, their supports, and the vessel 16 will be presented subsequently.

The use of materials for the pickup coils 12 having superconducting transition temperatures greater than 77K dictates the design of the system to a large degree. If the materials had lower superconducting transition temperatures, then a larger amount of insulation and a more powerful coolant than liquid nitrogen would be required. Experience has shown that achieving such lower temperatures in the container 14 is difficult, particularly if the walls 16 are flexible to permit reshaping of the container. The use of higher temperature superconductors allows liquid nitrogen cooling or even cooling with other liquefied gases or by mechanical means, without excessive insulation mass in the walls 16 of the container 14. Liquid nitrogen cooling is preferred, because liquid nitrogen is cheap, plentiful, and widely available in most hospitals and research facilities. It also has a relatively high heat of vaporization and therefore relatively high cooling efficiency. If cooling below the boiling point of liquid nitrogen, 77K at 1 atmosphere pressure, is required, the cooling is more difficult. The design of flexible insulated components is also much more difficult.

A detector 30 for each of the pickup coils 12 is placed within a second container 32. The detectors 30 are highly sensitive detectors of small electrical currents, and are preferably superconducting quantum interference devices (SQUIDs). The detectors 30 are formed of a material that is superconducting at temperatures below its superconducting transition temperature.

For some applications, the detectors 30 are preferably cooled to a temperature of near to absolute zero, such as below about 10K, and most preferably to liquid helium temperature, 4.2K. The detectors 30 must be operated in the superconducting state to provide maximum sensitivity. For some applications, it is preferably operated at a temperature close to absolute zero to minimize, as much as possible, thermally induced noise that degrades sensitivity in the detection circuit. In particular for many biomagnetic applications, the detectors 30 are operated near to absolute zero in order to reduce this noise in the circuit. It may not be sufficient for these applications to cool the detector just to a superconducting temperature, where that temperature is above about 30K, because thermally induced noise or noise arising from other sources at these higher temperatures may overwhelm the detected signal.

In other applications, however, it is not necessary to maintain the detector near to absolute zero, but only below its superconducting transition temperature.

SQUIDs have been fabricated from high temperature superconductors of the type discussed previously, an example being a SQUID made from $YBa_2Cu_3O_{7-x}$ material. Some high temperature SQUID detectors have noise levels, when operated at temperatures approaching or above 77K, substantially higher than those of SQUIDs operated at near absolute zero. These high temperature SQUIDs might be used where the magnetic signals to be measured are relatively large, as in magnetocardiographic measurements of the heart, for example. Low temperature SQUIDs, such as those made of niobium and operated near to absolute zero, might be used where the magnetic signals to be measured are relatively much smaller (and therefore more likely to be undetectable in the instrument noise of a high temperature SQUID), as in magnetoencephalographic measurements of the brain.

Thus, while in some preferred embodiments the SQUIDs are low temperature SQUIDs operating near absolute zero in liquid helium, the invention is not so restricted. The SQUIDs may be high temperature SQUIDs operated near, or above, 77K, where the instrument noise requirements permit. In either case, however, the SQUIDs are operated below their superconducting transition temperatures.

Returning to the discussion of the biomagnetometer shown in FIG. 1, to maintain the detectors 30 at temperatures near absolute zero, the second container 32 has an interior insulated wall 34 that permits it to be filled with liquid helium or other appropriate liquefied gas having a boiling point near absolute zero. Around the insulated walls 32 are heat shields 36 and an exterior insulated wall 38. The walls 34 and 38 are made of fiberglass, are good thermal insulators, and are vacuum impermeable. A vacuum line 40 is provided to communicate with the space between the walls 34 and 38, so that a vacuum may be drawn in this volume. Alternatively, a self-pumping getter can be used to maintain a vacuum. The detectors 30 are mounted on a support 42, which in turn is suspended through an opening in the top of the container 32. Heat shields 44 and the use of thermally insulating fiberglass in the support 42 insulate the detector 30 against heat loss through the opening. Wires 46 that act as electrical contacts from the detectors 30 to external instrumentation extend along the length of the support 42. The combination of the walls 34 and 38, the heat shields 98 and 44, and the vacuum between the walls 34 and 38 permits the detectors 30 to be maintained at a temperature near absolute zero without undue expenditure of coolant. The construction of such dewar vessels is described in greater detail in U.S. Pat. No. 4,773,952, whose disclosure is incorporated by reference. Alternatively, the detector may be cooled by a mechanical cooler, such as the type disclosed in U.S. Pat. No. 4,872,321, which disclosure is incorporated by reference.

The pickup coils 12 and the detectors 30 are electrically connected by a lead system 50. The leads of the system 50 extend from each pickup coil 12 to its respective detector 30, to convey signals from the pickup coil 12 to the detector 30. A lead 52 connects directly to the pickup coil 12 and is external to the second container 32, but connects to the interior of the second container 32 at a connector 56. From the connector 56, another lead 58 extends to a junction block 60, and another lead 62 extends from the junction block 60 to the detector 30. These various leads pass through several temperature environments, which will be described subsequently.

The leads 52, 58, and 62, as well as any elements of the connector 56 and junction block 60 that might carry current, are made of a material that is super conducting at the operating temperature of the system. Signals from each pickup coil 12 are conveyed to its detector 30 with no resistive loss in current, when these components are maintained in the superconducting state. The same $YBa_2Cu_3O_{7-x}$ material used for the coil 12 is preferred for use in these element and other high Tc superconductors are also operable.

A third container 70 encloses the lead system 50 and maintains it in the superconducting state. The lead 52 that extends from the pickup coil 12 to the connector 56 passes through the interior of the first container 14 for a short distance, and then through the interior of an elongated tube 72.

Figure 4:
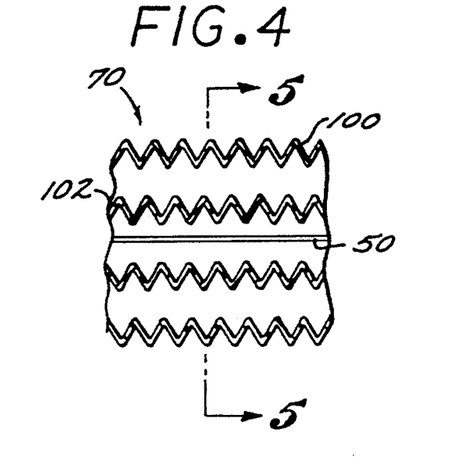
FIG. 4 is a side sectional view of a preferred flexible tube.
Figure 5:
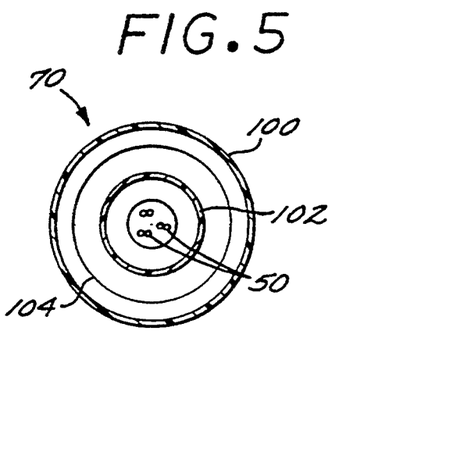
FIG. 5 is a cross sectional view of the tube of FIG. 4, taken along line 5—5.

The walls of the tube 72 are preferably, but not necessarily, flexible. FIGS. 4 and 5 illustrate the preferred construction of the container 70 in more detail. An outer wall 100 and an inner wall 102 are made of a corrugated nonmagnetic metal such as brass, beryllium, or copper. Such a corrugated construction permits limited flexibility of the walls and bending of the container 70 along its long axis. It permits a greater degree of elastic bending than possible with the metal itself. Such flexible construction is known for fabricating flexible bellows used in transferring cryogenic fluids. In one approach, the space between the outer wall 100 and the inner wall 102 is vacuum pumped to reduce conduction and convection heat loss and is wrapped with superinsulation 104. The space within the inner wall 102, holding the lead system 50, is filled with a liquefied gas, such as liquid nitrogen, to maintain the lead system 50 below its superconducting transition temperature during operation. The lead system may be formed from straight wires, if sufficiently flexible, or from the superconducting materials deposited upon a flexible substrate, such as a corrugated substrate, to achieve at least the same degree of flexibility as the outer and inner walls.

In the preferred approach, the interior of the tube 72 is continuous with, and communicates with, the interior of the first container 14. The tube 72 has a cryogenic liquid fill tube 75 near its uppermost region, so that a cryogenic liquid, most preferably liquid nitrogen, can be poured into the interior of the tube 72 and thence into the interior of the first container 14. In operation, the lead 52 is thereby maintained at a temperature below its superconducting transition temperature.

The lead 58, the junction block 60, and a lower portion of the lead 52 are contained within an insulated container 75 that is also part of the third container 70. The container 75 is attached to the underside of the second container 32, and has evacuated walls 78 to provide insulation sufficient for efficient thermal operation. A fill tube 80 permits liquid nitrogen to be poured into the interior of the container 76, so that the lead 58, the junction block 60, and the portion of the lead 62 within the container 76 are maintained at about 77K, below their superconducting transition temperatures. The upper portion of the lead 82 passes through a seal 82 into the interior of the second container 32, and is thence connected to the appropriate leads of the detector 30. The upper portion of the lead 62 is maintained at a temperature at which it is superconducting.

The connector 56 is provided between the leads 52 and so that they may be readily disconnected from each other. While it would be acceptable to have the lead system 50 be a continuous length of superconducting material, it is desirable to provide the connector 56 so that the portion of the lead system 50 exterior to the containers 32 and 75 may be readily disconnected. By this approach, the entire pickup coil array may be removed and replaced with another array, without requiring that the detector SO be warmed. The connector 56 may be a plug connector that seals against loss of liquid gas, an inductively coupled connector, or other acceptable type known in the field of cryogenics.

Figure 2A:
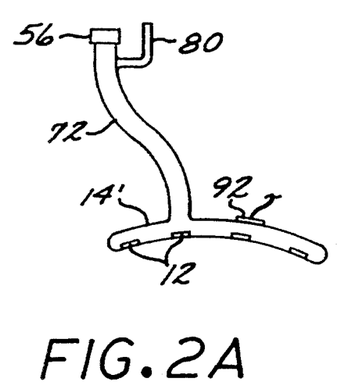
FIGS. 2A-C are elevational views of several configurations of pickup coil and container operable with the present invention.
Figure 2B:
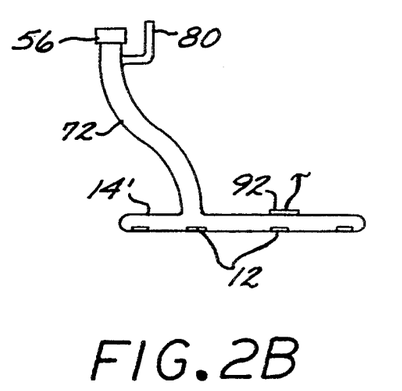
Figures 2C, 3:
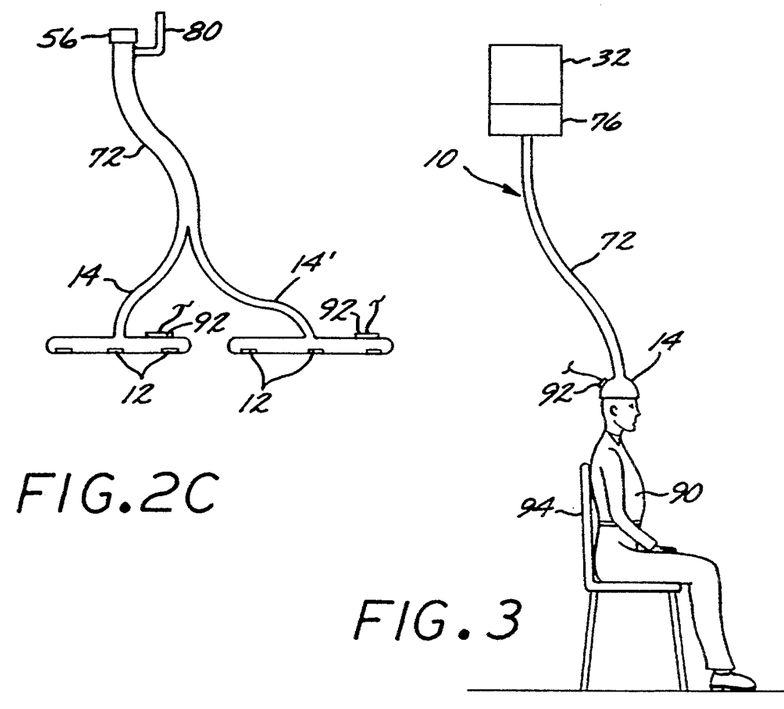
FIG. 3 is a perspective view of the operational arrangement of the apparatus of FIG. 1.

FIGS. 1, 2A, 2B, and 2C show some alternative configurations for an array of pickup coils 12 and the corresponding first container 14. In FIG. 1, the container 14 is configured to generally fit over the skull of a subject, somewhat like a cap, so that the array of coils 12 may be placed at many different locations relative to the brain of the subject. In FIG. 2A, the coils 12 and container 14 are in a gently curved form that could be placed against the body, as for example over the chest to sense magnetic fields produced by the heart. In FIG. 2B the coils 12 and container 14 are depicted in a flat form. FIG. 2C illustrates a form having two arrays of pickup coils 12 and 12', located respectively in two containers 14 and 14'. This configuration is suited for simultaneous measurements of different parts of the body, as, for example, two separate portions of the brain, or the peripheral nervous system and the brain. In each case, there is provided a tube 72, fill tube 80, and one side of the connector 56. Any or all of these containers may be made partly or entirely flexible, as will be described subsequently.

It will be appreciated that these various configurations are presented as illustrative, and that custom configurations can be designed and built using the techniques described herein. The important point is that, using the approach of the invention, the detector, which may require an operational temperature near absolute zero, is physically separated from the pickup coils, which need only be operated in the superconducting state and not necessarily near absolute zero, and connected with a lead system that also need only be operated in the superconducting state and not necessarily near absolute zero. Using high temperature superconductors having superconducting transition temperatures above 77K, the structure used to maintain the pickup coil and the lead system at or below the superconducting temperature is much simpler and less bulky than the structure used to maintain the detector near absolute zero.

FIG. 3 illustrates the use of the biomagnetometer 10, constructed according to the prior description and as shown in FIG. 1. A subject 90 sits in a chair 94 with the first container 14 on the subject's head, and with an array of pickup coils therein positioned around the head. The second container $2 and container 75 are mounted above and some distance from the subject 90. The flexible tube 72 extends from the first container 14 to the containers 32 and 76.

This approach has important advantages over the prior approach, which is generally illustrated in FIG. 1, of U.S. Pat. No. 4,793,355, whose disclosure is incorporated by reference. In this prior approach, the pickup coils were necessarily located within the rigid, bulky dewar, and as a result could not be easily moved. The ability to arbitrarily position the pickup coils was also significantly limited. In the present approach, the pickup coils are located close to the body of the subject, resulting in greater signal strength and hence higher resolution and improved signal-to-noise ratio. A large array of pickup coils 12 can be placed in proximity to the subject, and on all sides. This capability is expected to be of great significance in advanced techniques now under development for correlating signals obtained simultaneously from arrays of pickup coils. The flexible tube 72 permits the subject to move around slightly, thereby avoiding undue constraints that might cause unwanted responses in the brain. The use of a connector 56 between the tube 72 and the lead 58 allows the entire tube 72, array of pickup coils 12, and first container 14 to be disconnected and replaced with another unit without bringing the detector 30 to ambient temperature, which was impossible with the apparatus illustrated in the '355 patent.

The '355 patent discloses an approach for automatically tracking the position of the pickup coil and the subject. This approach is readily applied in conjunction with the present invention. Each of the first containers 12 shown in FIGS. 1–3 includes a position monitoring sensor 92 that is used in conjunction with the apparatus disclosed in the '355 patent to monitor the position of the coil array.

As the technology of superconductors advances, it is possible that materials which are superconducting at even higher temperatures, up to ambient temperature, will be discovered. The present invention is operable with such materials used in the pickup coils and the conducting portions of the lead system 50. In this instance, insulation for the containers that contain the lead system 50 is greatly reduced and may not be required, except where the leads are brought to lower temperatures for connection with the detector 30.

Figure 6:
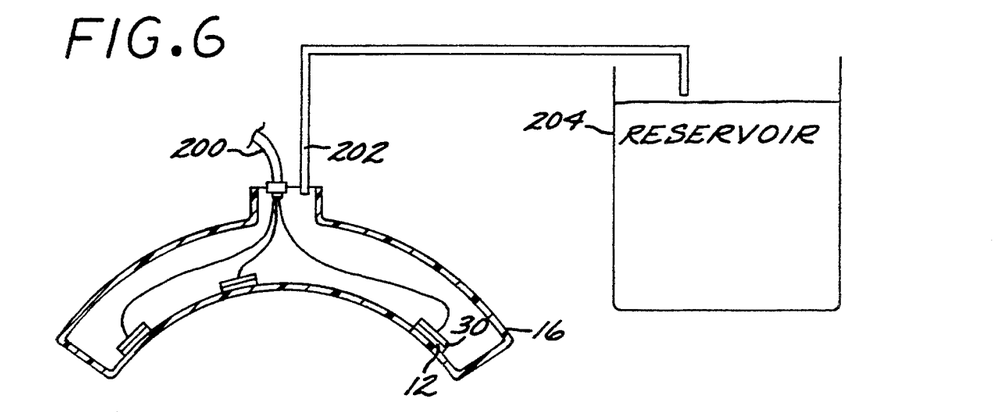
FIG. 6 is a side sectional view of a pickup unit made in accordance with the invention.
Figure 7:
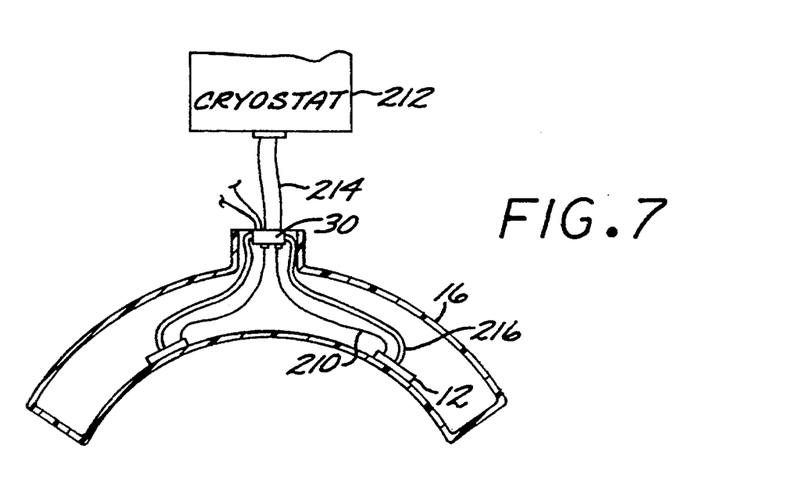
FIG. 7 is a side sectional view of another embodiment of the pickup unit.

FIGS. 6 and 7 illustrate two designs for the vessel 16 wherein all or part of the vessel wall is flexible. In FIG. 6, each pickup coil 12 within the vessel 16 has a detector 30, preferably a superconducting quantum interference device, integral with the pickup coil 12. The output signals of the detectors 30 are transmitted to conventional ambient temperature electronics (not shown) through a cable 200. The interior of the vessel 16, including the integral pickup coil/detector unit, is cooled to less than the superconducting transition temperatures of the super conductor materials in the pickup coil 12 and the detector 30 by a stream of coolant 202 supplied from a reservoir 204. The coolant can be either a liquid, such as liquid nitrogen, or a refrigerated gas, such as gaseous nitrogen produced from liquid nitrogen and which has a temperature below that required. The higher the required temperature, the less difficult is the maintenance of that temperature using a refrigerated gas coolant.

In FIG. 7, all of the detectors 30 are placed at a central location within the vessel 16, with superconducting wires 210 leading to the pickup coils 12. The interior of the vessel 18 is cooled by conduction from a cryostat 212, such as that disclosed in U.S. Pat. No. 4,872,321. An insulated conducting wire such as a copper wire bundle 214 extends from the cold region of the cryostat 212 to the vessel 16. The detectors 30 are preferably mounted directly in contact with the end of the copper wire bundle 214, and are cooled by conduction of heat from the detectors 30 to the cryostat 212. The pickup coils 12 are cooled by individual copper wire bundles 216 extending from the bundle 214 to the individual pickup coils 12.

Figure 8:
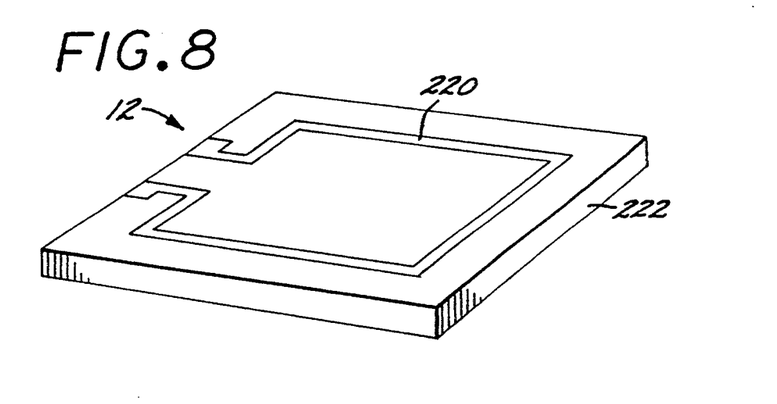
FIG. 8 is a perspective view of a pickup coil formed on a substrate.

The cooling and pickup coil/detector arrangements of FIGS. 6 and 7 may be used in an appropriate intermixed manner, with, for example, the cooling approach of FIG. 8 used with the detector placement of FIG. 7. The selection of particular configurations is usually made with the cooling requirements in mind. The higher the Tc values of the materials used in constructing the pickup coils and detectors, the less cooling power is typically required.

Figure 9:
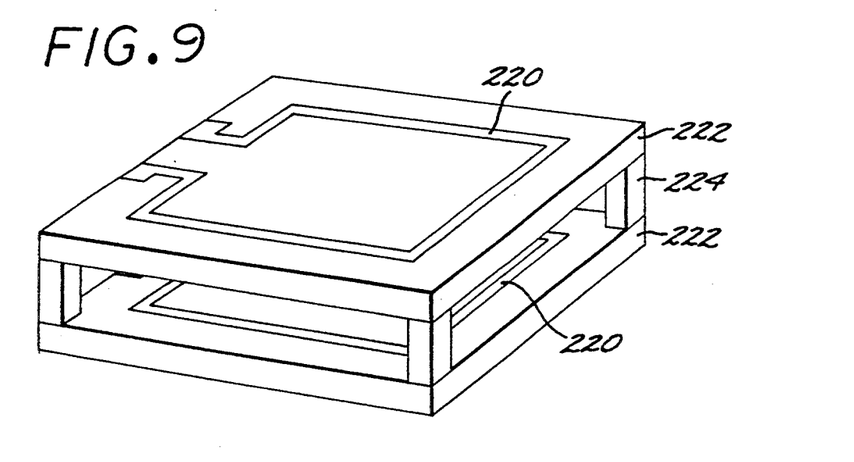
FIG. 9 is a perspective view of a gradiometer formed on two substrates.

In all of the embodiments discussed herein, the pickup coils 12 are preferably formed as thin film depositions on a substrate. FIG. 8 illustrates such a pickup coil 12 deposited as a thin film loop 220 on a substrate 222. The material of the thin film loop 220 is a high-Tc superconductor, preferably $YBa_2Cu_3O_{7-x}$, where x is 0.1–0.2 or less, and the substrate 222 is compatible with the superconductor, preferably (100) $LaAlO_3$. The thin film loop 220 is prepared by patterning the substrate 222 in a conventional fashion and then depositing the superconductor, typically by sputtering. The procedures for the deposition of high temperature superconductors onto substrates are well known in the art, see the publications listed in the following paragraph. A gradiometer or more complex form of pickup coil 12 can be prepared by superimposing two of the substrates 222 with interconnected loops 220 deposited thereon, either in direct contact or separated by standoffs 224, see FIG. 9.

Figure 10:
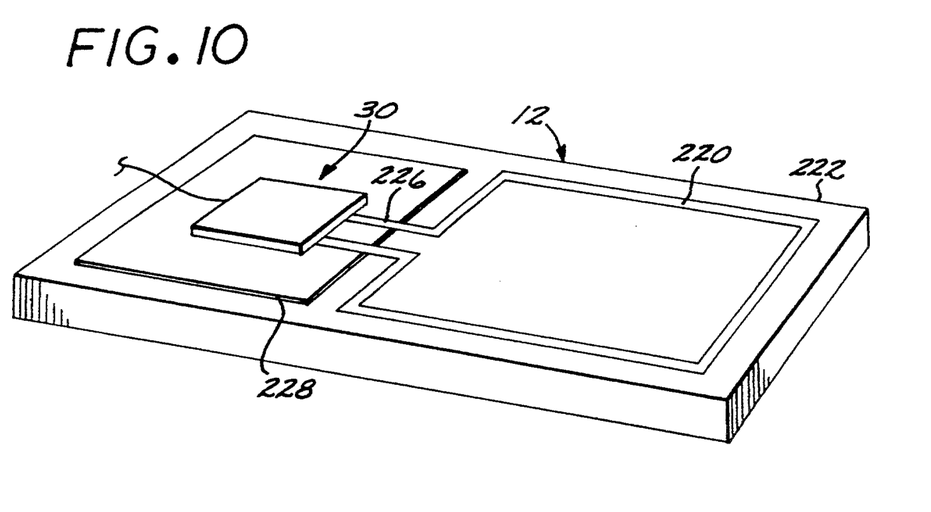
FIG. 10 is a perspective view of a pickup coil and a SQUID formed on a substrate.

The embodiment discussed in reference to FIG. 6 has the pickup coil 12 and the detector 30 on a single supporting substrate, and an implementation of this approach is depicted in FIG. 10. A SQUID detector 30 is deposited on the same substrate 222 as the thin film loop 220 that operates as the pickup coil 12. Connecting conductors 226 of the same high-Tc superconducting material connect the thin film loop 220 to the detector 30. A shielding layer 228 of the same high-Tc superconducting material may be deposited underlying the SQUID detector 30 to shield it from the magnetic field. Techniques for depositing thin film SQUID detectors 30 and thin film loops 220 on substrates 222 are known in the art, see for example, U.S. Pat. No. 5,134,117; J. Gao et al., "Controlled preparation of all high-Tc SNS-type edge junctions and DC SQUIDs", *Physica*, C171, pages 126–130 (1990); R. Gross et al., "Low Noise $YBa_2Cu_3O_7$ grain boundary junction dc SQUIDs", *Appl. Phys. Lett.*, vol. 57(7), pages 727–729 (Aug. 13, 1990); K. P. Daly et al., "Substrate step-edge $YBa_2Cu_3O_7$ rf SQUIDs", *Appl. Phys. Lett.*, Vol. 58(8), pages 548–545 (Feb. 4, 1991); and M. S. DiIorio et al., "Practical high Tc Josephson junctions and dc SQUIDs operating above 85K", *Appl. Phys. Lett.*, Vol. 58(22), pages 2552–2554 (June 1991).

Although in FIG. 10 only a single thin film loop 220 and its associated detector 30 are shown, thin film deposition technology permits large numbers of pickup coils 12 and, where desired, associated detectors SO to be deposited on a single substrate 222. This technology also permits the production of numbers of pickup coils 12 that are placed at different locations within the vessel 16.

Figure 11:
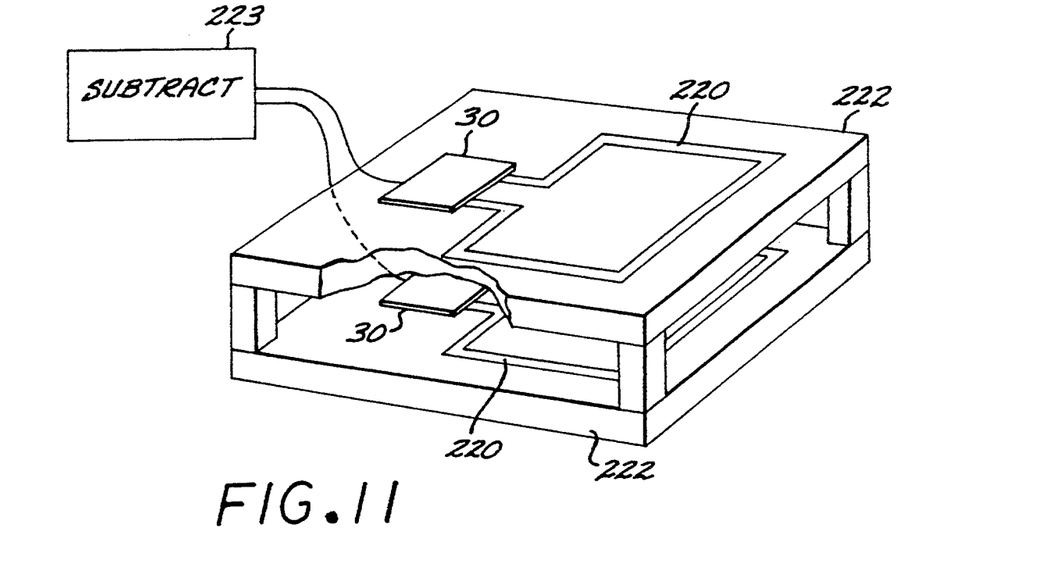
FIG. 11 is a perspective view of a gradiometer made of a pickup coil and SQUID on each of two substrates.

Another embodiment, shown in FIG. 11, utilizes two substrates 222 vertically displaced from each other, with a pickup coil 220 and its associated SQUID 30 on each of the substrates 222. The output of one of the SQUIDs 30 is subtracted from the other in a subtraction circuit 223. The difference between the two SQUID signals is a measure of the magnetic field gradient.

It is important that the vessel 16 be properly insulated so that an unacceptably large heat flow into the vessel 16 from the surroundings will not occur. That heat flow would not only drive the superconductors into the normal state, but would also result in discomfort for the subject if a portion of the heat flows from the subject's body. Several configurations have been identified as permitting the pickup coils to be placed closely to the subject while also providing adequate insulation.

Figure 12:
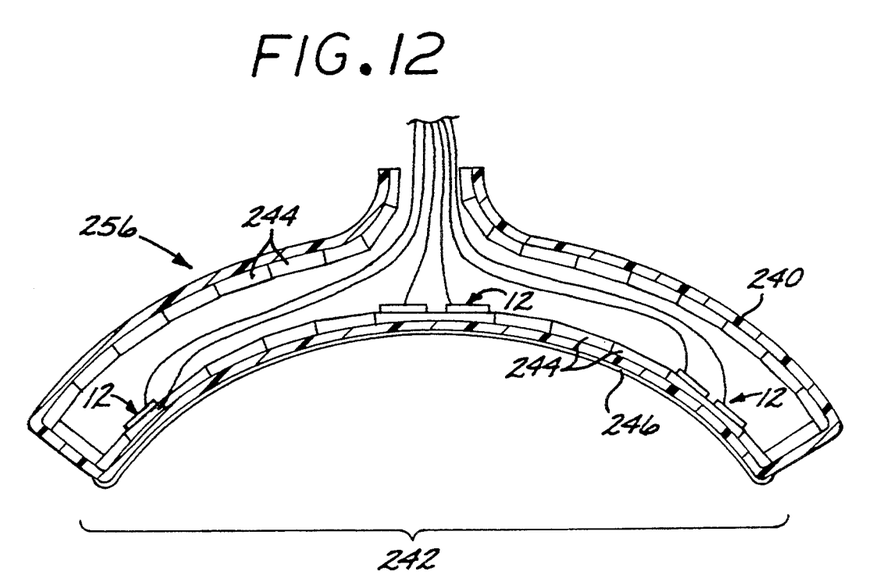
FIG. 12 is a side sectional view of an insulated vessel.

FIG. 12 depicts one preferred configuration of the vessel 15, termed the pickup unit 256. The pickup unit 256 has a wall 240 made of a flexible material that maintains its physical integrity at the cryogenic temperature maintained within the vessel 16. A preferred material of construction for the wall 240 is a layered structure formed of sheets of a thin polymeric material such as mylar, and layers of cloth. The pickup coils 12 are affixed to the interior of the wall 240, along a region termed the contact region 242. The pickup coils 12 are placed onto at least one, preferably at least two, and most preferably a plurality of, individual substrates that are affixed to the wall 240 in the contact region 242. The individual substrates and pickup coils are spaced apart a sufficient amount that the wall 240 retains its flexibility.

Packets of insulation 244 such as pieces of polystyrene foam are affixed to the interior of the wall 240. The packets of insulation are fixed to the wall 240 to form a continuous, but flexible, layer in regions apart from the contact region 242, and are interspersed between the pickup coils 12 in the contact region 242. The pickup coils 12 are not insulated from the interior of the vessel 16 by overlying packets of insulation, because the pickup coils 12 must be cooled to their operating temperatures by conduction to the interior of the vessel 16. Individual small packets or pieces of foam are used, rather than a large or continuous piece, so that the vessel retains its flexibility. A portion of the wall 240, away from the contact region 242, could be made of a rigid insulator material, as long as the rigid portion does not prevent the flexible contact region 242 from being operable.

The reduction of heat conduction through the contact region 242 is important, because such heat input has the most direct effect in driving the superconductors of the pickup coils 12 normal, and because that heat comes directly from the body of the subject against which the contact region 242 is pressed, possibly making the subject uncomfortable. To reduce the heat loss through the contact region 242 even further, a number of layers 246 of flexible plastic such as mylar or Kevlar(R) are sealed over the exterior surface of the contact region 242. The edges of the layers 246 are sealed against the wall 240 in a dry environment, to permit insulating air to remain between the layers 246 but to exclude moisture that could freeze to form ice during use of the vessel 16.

Figure 13:
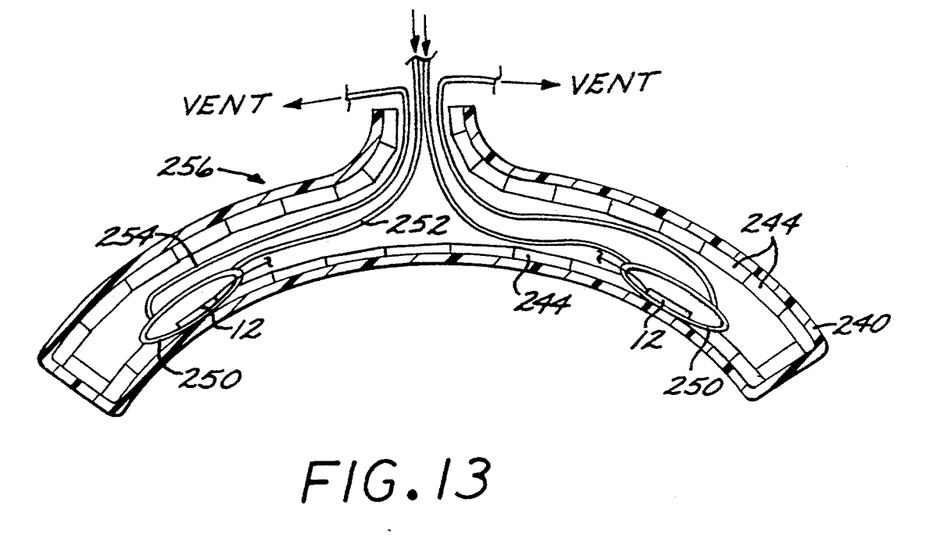
FIG. 13 is a side sectional view of another embodiment of the insulated vessel.

An alternative approach, shown in FIG. 13, places each pickup coil 12 in its own insulated housing 250. The insulated housing 250 is constructed from foam insulation such as polystyrene, hollowed out to receive the pickup coil 12. Packets of insulation 244 are affixed to the other interior surfaces of the wall 240. A preferred cooling approach is to direct liquid or gaseous coolant into the interior of the housing 250 through coolant lines 252 and vent the interior of the housing 250 with vent lines 254.

Figure 14:
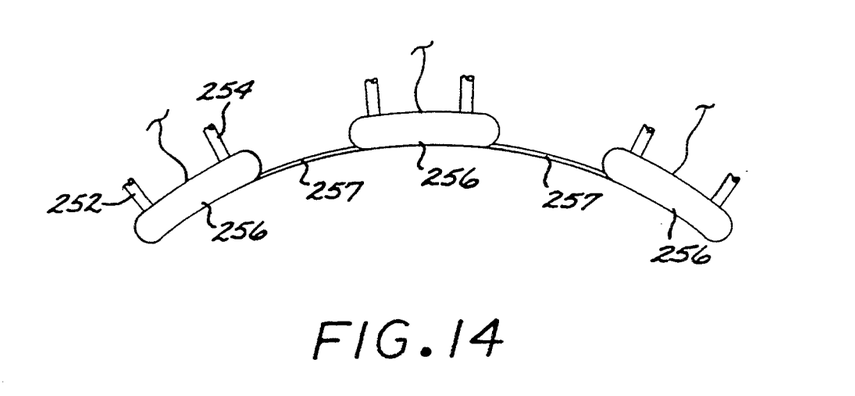
FIG. 14 is an elevational view of three integrated pickup units Joined together in an array.

The pickup units 256 can be joined together in arrays. The pickup coils 12 and the detectors 30 are both made from superconductors having a superconducting transition temperature of 77K or above. In the embodiment of FIG. 14, several of the pickup units 256 (in this case with both the pickup coil and the detector therein) are connected together with pieces of tape or sewn strips 257 to form a conformable array that can be assembled in the field, by doctors or scientists to form an "ad hoc" array useful for a particular investigation.

Figure 15:
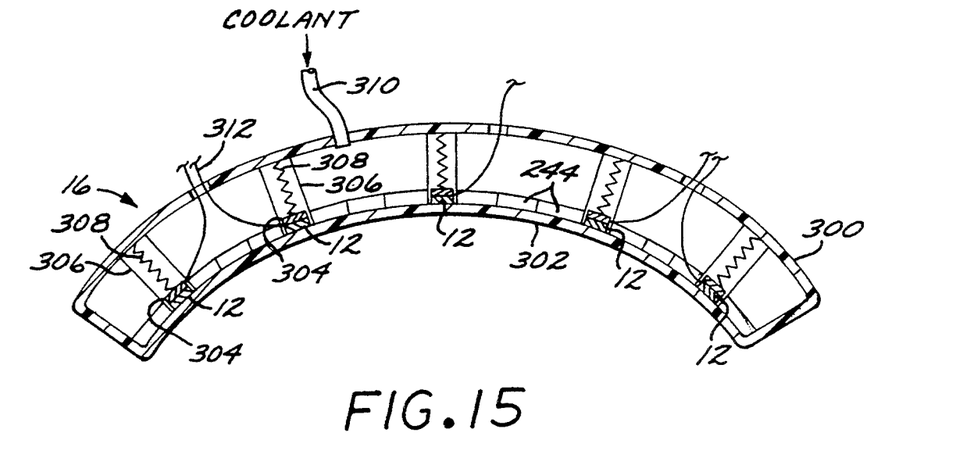
FIG. 15 is a sectional view of an alternative approach in accordance with the invention.

FIG. 15 illustrates another embodiment of the device utilizing a flexible wall for the vessel containing the coolant. The vessel 15 of FIG. 15 includes a rigid wall portion 300 that defines the general configuration of the vessel, here in the form of a helmet to be placed over the head of the subject. A flexible wall portion 302 of the vessel 16 is adapted for contact with the body of the subject, and closes the vessel 15. The flexible wall portion 302 is constructed in the same manner as the flexible walls discussed previously.

The pickup coils 12, preferably made of high temperature superconductors, are attached to pickup coil supports 904. The pickup coil supports 304 are slidably mounted in support tubes 306 fixed to the rigid wall portion 300, with the axis of each tube 306 directed generally inwardly. An inwardly-directed biasing force, provided by a spring 308 in each of the support tubes 306, against the coil supports 904 forces the supports 304 and thence the pickup coils 12 inwardly against the inner wall of the flexible wall 302. The biasing force causes the pickup coil 12 to conform to the shape of the flexible wall 302. When the apparatus is placed into contact with the body of the subject, the flexible wall 302 conforms to the shape of the body. The pickup coils 12 in turn conform to the shape of the flexible wall 302. With this arrangement, the pickup coils 12 may be conformed to fit closely to the shape of the body of the subject.

Coolant is provided to the interior of the vessel 16 through a coolant tube 310, like that discussed previously. Signals from the pickup coils 12 can be processed by integrally mounted SQUID detectors, as in this illustrated approach, and the output signals transmitted on leads 312. Alternatively, the signals from the pickup coils 12 can be transmitted to remotely positioned SQUID detectors maintained at colder temperatures. Packets of insulation 244, like those discussed previously, are affixed to the interior of the flexible wall 302, and optionally the rigid wall 300.

Figure 16:
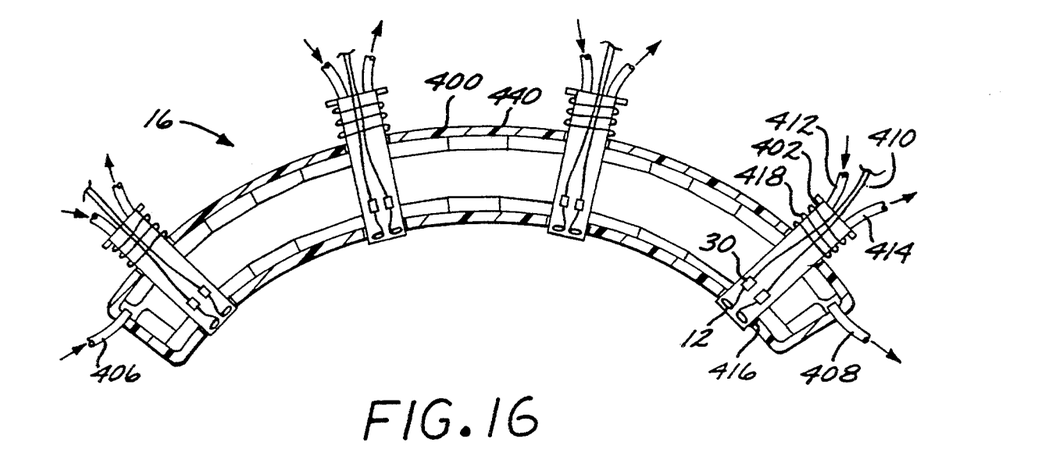
FIG. 16 is a sectional view of a flexible sensor utilizing multiple spring-mounted detector capsules.

FIG. 16 depicts another embodiment that incorporates several of the previously discussed concepts. The vessel 16 includes a rigid support structure 400 that supports at least one, and preferably several, capsules 402. The walls of the structure 400 are formed of a thermally insulating, nonmagnetic material such as fiberglass, and optionally include internal or external insulating foam packets 404. The interior of the structure 400 is cooled by a flow of coolant, such as a liquefied gas or a cooled gas, from an input line 405, and exhausted by an output line 408. The structure 400 may be provided in any shape, and is here illustrated in the form of a helmet that can fit over the head of a subject.

The capsules 402 each contains at least one pickup coil 12 and, preferably, a detector 30 such as a SQUID for each of the pickup coils 12. Signals from the pickup coil are detected by the detector 30, and the output signals of the detector 30 are transmitted to external electronics through pairs of leads 410. Each capsule 402 may be cooled internally by a flow of coolant, such as a liquefied gas or a cooled gas, from an input line 412 and exhausted by an output line 414. Thus, the capsules may be cooled by conduction from the coolant in the structure 400, directly by coolant supplied by the input line 412, or a combination of the two. The capsules 402 are made from a thermally insulating material such as fiberglass. However, if cooling by conduction from the coolant in the structure 400 is relied upon, the portion of the wall of the capsule 402 contacting the interior of the structure 400 may be made of a thermally conducting material, or have conducting inserts through the wall.

Each capsule 402 is slidably mounted in the wall of the structure 400, with seals 418 preventing leakage of the coolant within the structure 400, if any. Each capsule 402 is resiliently biased inwardly by a spring 418 reacting between the structure 400, preferably its exterior wall, and the capsule 402. This approach permits the vessel 16 having the single-sized structure 400 to be operable for subjects of different sized and shaped heads, and for persons having bandages and the like. Stated alternatively, the inner surfaces of the capsules together constitute a flexible contact face whose position locally adjusts to the underlying body shape responsive to the spring force. The structure 400 is placed over the head and the capsules 402 allowed to relax inwardly in response to the spring force, with the inner end of each capsule 402 contacting the body of the subject. Measurements are then taken in the normal fashion.

The present approach produces completely new results unavailable with conventional dewar-based biomagnetometer systems. The fabrication of both the pickup coils 12 and the detectors 30 from high temperature superconductors (having Tc of 77K or more) permits sufficient insulation to be provided using conventional foam, non-vacuum insulation material such as polystyrene. The coolant can be a readily available, inexpensive coolant such as liquid or refrigerated gaseous nitrogen. In some forms, the entire integrated pickup unit 256 becomes a package weighing less than one pound that can be held in the palm of the hand, as compared with conventional biomagnetometers typically weighing over 70 pounds and being over 4 feet long. The performance of the integrated pickup unit 256 may be limited in some applications by the inability to cool the detector to near-absolute zero to suppress noise, but the convenience of the unit more than makes up for this limitation by providing increased convenience for many other uses.

Although a particular embodiment of the invention has been described in detail for purposes of illustration, various modifications may be made without departing from the spirit and scope of the invention, Accordingly, the invention is not to be limited except as by the appended claims.

What is claimed is:

1. A biomagnetometer, comprising:
 a magnetic field sensor unit, the sensor unit including
  a magnetic field pickup coil made of a material having a superconducting transition temperature;
 vessel means for containing the magnetic field sensor unit, the vessel means including
  a flexible contact face adapted for contacting to a subject whose biomagnetism is to be measured, with the magnetic field sensor unit mounted in the interior of the vessel means adjacent to the flexible contact face, and
  rigid support structure means for defining the general configuration of the vessel means, the flexible contact face being attached to the support structure means;

insulation means at the flexible contact face of the vessel means for preventing excessive heat flow through the flexible contact face;

means for cooling the pickup coil to a temperature of less than its superconducting transition temperature; and detector means for receiving an output signal of the pickup coil and for measuring the magnitude of magnetic fields sensed by the sensor unit.

2. The biomagnetometer of claim 1, wherein the vessel means includes a flexible bag.

3. The biomagnetometer of claim 1, wherein the flexible contact face includes a layered structure of a thin polymeric material and cloth.

4. The biomagnetometer of claim 1, wherein the insulation means includes packets of insulation affixed to an interior wall of the vessel means.

5. The biomagnetometer of claim 1, wherein the detector means includes a superconducting quantum Interference device mounted within the vessel means.

6. The biomagnetometer of claim 1, wherein the detector means includes a superconducting quantum interference device mounted outside the vessel means.

7. The biomagnetometer of claim 1, wherein the pickup coil is formed of a material having a superconducting transition temperature of at least about 77K.

8. The biomagnetometer of claim 1, wherein the sensor unit further includes a magnetic field pickup coil support upon which the magnetic field pickup coil is mounted.

9. The biomagnetometer of claim 1, wherein the support structure means comprises a first portion of a wall of a vessel and the flexible contact face comprises a second portion of the wall of the vessel, the support structure means and the flexible contact face together comprising the wall of the vessel containing the magnetic field sensor unit therein.

10. The biomagnetometer of claim 1, further including biasing means for forcing the pickup coil against an interior side of the flexible wall portion.

11. The biomagnetometer of claim 1, wherein the vessel means comprises a support structure, and at least two capsules, each capsule containing at least one pickup coil, with each capsule resiliently mounted to the support structure.

12. A biomagnetometer, comprising:

a plurality of pickup units, each pickup unit comprising a magnetic field sensor unit, the sensor unit including a magnetic field pickup coil made of a material having a superconducting transition temperature, vessel means for containing the magnetic field sensor unit, the vessel means including a contact face adapted for contacting to a subject whose biomagnetism is to be measured, with the magnetic field sensor unit mounted in the interior of the vessel means adjacent to the contact face, and insulation means at the contact face of the vessel means for preventing excessive heat flow through the contact face, means for mechanically interconnecting the plurality of pickup units to form a flexible array that is conformable to the shape of a body of a subject, the means for mechanically interconnecting permitting the plurality of pickup units to flex relative to each other; and detector means for receiving an output signal of the pickup coil and for measuring the magnitude of magnetic fields sensed by the sensor units.

13. The biomagnetometer of claim 12, wherein the vessel means of at least some of the pickup units includes a flexible bag.

14. The biomagnetometer of claim 12, wherein the detector means includes a superconducting quantum interference device for each of the pickup coils, the superconducting quantum interference device being located within each of the respective vessel means.

15. The biomagnetometer of claim 12, wherein each sensor unit further includes a magnetic field pickup coil support upon which the magnetic field pickup coil is mounted.

16. The biomagnetometer of claim 12, further including means for cooling the pickup coils to a temperature of less than their superconducting transition temperatures.

17. The biomagnetometer of claim 12, wherein the pickup coils are formed of materials having a superconducting transition temperature of at least about 77K.

18. The biomagnetometer of claim 12, wherein the contact face is formed of a layered structure of a thin polymeric material and cloth.

19. The biomagnetometer of claim 12, wherein the insulation means includes packets of insulation affixed to an interior wall of the vessel means.

20. The biomagnetometer of claim 12, wherein the means for mechanical interconnecting is a flexible connector.

* * * * *